United States Patent [19]

Palmer et al.

[11] 4,173,708

[45] Nov. 6, 1979

[54] PURIFICATION OF 4,4'-BENZOPHENONEDICARBOXYLIC ACID

[75] Inventors: Louis R. Palmer, Morristown; James T. Karo, Madison, both of N.J.

[73] Assignee: Allied Chemical Corporation, Morris Township, Morris County, N.J.

[21] Appl. No.: 846,758

[22] Filed: Oct. 31, 1977
(Under 37 CFR 1.47)

[51] Int. Cl.$^2$ ............................................. C07C 65/20
[52] U.S. Cl. .................................................. 562/460
[58] Field of Search ......................... 260/517; 562/460

[56] References Cited

U.S. PATENT DOCUMENTS

| | | | |
|---|---|---|---|
| 2,862,963 | 12/1958 | Fuchs et al. | 260/525 |
| 3,197,499 | 7/1965 | McCracken | 260/475 |
| 3,215,734 | 11/1965 | Katzschmann | 260/525 |
| 3,370,088 | 2/1968 | Lese | 260/517 |
| 3,448,146 | 6/1960 | Lese et al. | 260/525 |
| 3,510,513 | 5/1970 | McCracken | 260/517 |
| 3,577,457 | 5/1971 | Schulz | 260/517 |
| 3,849,489 | 11/1974 | Rudzki | 260/525 |

FOREIGN PATENT DOCUMENTS 252324 3/1970 U.S.S.R. .
333164 3/1972 U.S.S.R. .

OTHER PUBLICATIONS

Wiberg, *Laboratory Technique in Org. Chemistry*, p. 112, (1960).

*Primary Examiner*—Jane S. Myers
*Attorney, Agent, or Firm*—Robert A. Harman; Robert J. North

[57] ABSTRACT

A process is described for purifying 4,4'-benzophenonedicarboxylic acid, useful in preparing thermoplastic polyesters yielding molded articles having high impact strength, wherein the acid contains aromatic monocarboxylic acid genetic impurity, which comprises the steps of (a) mixing the impure 4,4-benzophenonedicarboxylic acid with aqueous ammonium hydroxide solution, containing about 28 weight percent or less of ammonia in a weight ratio of solution to acid of about 5:1 to 100:1, thereby forming a solution of the diammonium salt of the aromatic dicarboxylic acid;

(b) mixing the resultant solution with an inert water-soluble organic liquid which is a non-solvent for the diammonium salt, in a weight ratio of organic liquid to solution not greater than about 20:1, thereby precipitating the diammonium salt of the acid;

(c) separating the diammonium salt from the solution; and (d) recovering the aromatic dicarboxylic acid from the diammonium salt.

5 Claims, No Drawings

PURIFICATION OF 4,4'-BENZOPHENONEDICARBOXYLIC ACID

BACKGROUND OF THE INVENTION

1. Field of the Invention

This invention relates to a process for purifying 4,4'-benzophenonedicarboxylic acid, useful in preparing thermoplastic polyesters.

2. Brief Description of the Prior Art

It is known in the art that in order to optimize the properties of thermoplastic polyesters to be used for making shaped articles, it is usually necessary to employ substantially pure starting materials to avoid crosslinking during the molding process. This is especially true for aromatic dicarboxylic acid-based polyesters which are to be shaped into articles for use in applications requiring high impact resistance, e.g. safety glass, windows, housing for chemical machinery and the like.

Aromatic dicarboxylic acids used in preparing polyesters, are normally obtained by oxidation of the precursor dialkylaromatic hydrocarbon. So obtained, they are generally contaminated with genetic impurities, particularly, incompletely oxidized aromatic monocarboxylic acids. In the case of 4,4'-benzophenonedicarboxylic acid, a common genetic impurity is 4-alkyl-4'-benzophenone monocarboxylic acid. Monocarboxylic acid genetic impurities contained in the final dicarboxylic acid product must be removed before use in polymerization to insure desirable properties of the final polymer. However, separation of the pure diacid from its genetic monocarboxylic acid impurities often is a tedious and difficult task.

Prior art processes for the purification of 4,4'-benzophenonedicarboxylic acid are known and are described in the following patents: U.S. Pat. No. 3,197,499 (McCracken, et al., 1965) which involves preparation of the dimethyl ester; U.S. Pat. No. 3,510,513 (McCracken, et al., 1970) which uses hydrogen and a hydrogenation catalyst at high temperature and high pressure; U.S. Pat. No. 3,370,088 (Lese, et al., 1968) which involves high pressure extraction of impurities with methanol or acetone; U.S. Pat. No. 3,577,457 (Schultz, 1971) which involves heating with methanol or ethylene glycol to remove impurities; and U.S. Pat. No. 3,448,146 (Lese, et al., 1969) which involves forming a carbonyl adduct of the impurities.

However, the above methods possess the disadvantages of requiring either repeated applications for obtaining high purity, or expensive high pressure equipment, high temperatures, expensive organic solvents, or conversion of the diacid to the diester necessitating a subsequent saponification step, all of which render the methods expensive, hazardous or time consuming on an industrial scale.

A process for purifying 2,6-naphthalenedicarboxylic acid is disclosed in U.S.S.R. Patent No. 333,164 (1972), wherein crude 2,6-naphthalene dicarboxylic acid is purified from isomeric naphthalene dicarboxylic acids by dissolving alkali salts of these acids in an aqueous alcoholic medium containing up to 80 weight percent ethanol or ethylene glycol, followed by saturation of the resulting solution with ammonia gas and separation of the desired product from the resulting precipitate. However, the process requires the use of large amounts of expensive organic solvents.

Related methods are known for the purification of low molecular weight aromatic dicarboxylic acids, such as terephthalic acid, but because of large differences in melting points and solubilities between low and high molecular weight aromatic dicarboxylic acids, it is generally not predictable that these related methods will also be applicable to high molecular weight acids.

Representative purification methods for terephthalic acid containing impurities such as para-toluic acid and isophthalic acid, obtained by oxidation of commercial p-xylene by means of air or nitric acid are described in the following patents: U.S. Pat. No. 3,215,734 (Katzschmann, 1965) in which a crude oxidation mixture is suspended in a water-dimethylformamide mixture, ammonia gas is bubbled through forming the soluble ammonium salt of terephthalic acid at about 90° to 100° C., and water is then distilled off until the ammonium salt of terephthalic acid precipitates; U.S. Pat. No. 3,849,489 (Rudzki, 1971) in which a two-step process is utilized forming an ammonium salt of crude terephthalic acid and then volatilizing off impurities by heating at a temperature of 280° to 290° C., and then decomposing the ammonium salt to terephthalic acid, wherein the process is then repeated but the separation step is accomplished by bubbling ammonia into the solution to separate the ammonium salt of terephthalic acid, which is recovered and converted into terephthalic acid; U.S. Pat. No. 2,862,963 (Fuchs, et al., 1958) in which a crude mixture of acids is suspended in a liquid medium consisting of one or more alcohols containing up to six carbon atoms, saturating the mixture with gaseous ammonia at elevated temperatures thereby forming soluble ammonium salts of monocarboxylic acids and the insoluble ammonium salt of terephthalic acid.

Russian Patent No. 252,324 (1970) describes the separation of terephthalic acid from the products of the thermocatalytic regrouping of the potassium salts of benzenecarboxylic acids by dissolving the potassium salts in aqueous solution, adding ammonia to form the diammonium salt of terephthalic acid and preferentially precipitating it with the addition of acetone. However, the method is not described as being applicable to a mixture of the free acids containing a substantial amount of aromatic monocarboxylic acid impurity.

While the above related methods are useful for the purification of terephthalic acid, no suggestion is made that the methods are useful for the purification of 4-4'-benzophenonedicarboxylic acid.

SUMMARY

In accordance with this invention there is provided a process for purifying 4,4'-benzophenonedicarboxylic acid containing aromatic monocarboxylic acid genetic impurity which comprises the steps of (a) mixing the impure 4-4'benzophenonedicarboxylic acid, with aqueous ammonium hydroxide solution, containing about 28 weight percent or less of ammonia, in a weight ratio of solution to acid of about 5:1 to 100:1 thereby forming a solution of the ammonium salt of the aromatic dicarboxylic acid;

(b) mixing the resultant solution with an inert water-soluble organic liquid which is non-solvent for the ammonium salt, in a weight ratio of organic liquid to solution not greater than about to 20:1, thereby precipitating the ammonium salt of the acid;

(c) separating the ammonium salt from the solution; and (d) recovering the aromatic dicarboxylic acid from the ammonium salt.

DETAILED DESCRIPTION OF THE INVENTION AND PREFERRED EMBODIMENTS

The process of this invention is useful for purifying 4,4'-benzophenonedicarboxylic acid containing aromatic monocarboxylic acid genetic impurity.

Aromatic dicarboxylic acids are usually prepared by oxidation of a precursor dialkyl aromatic hydrocarbon and the crude mixture that is obtained contains undesirable impurities which are usually difficult and tedious to remove. For example, in the preparation of 4,4'-benzophenonedicarboxylic acid from the chromic acid oxidation of 4,4'-dimethylbenzophenone, the usual impurities obtained in the final product are unreacted dialkyl aromatic hydrocarbon 4,4'-dimethylbenzophenone, benzophenone-4-carboxylic acid resulting from the oxidation of 4-methylbenzophenone present as an impurity in 4,4'-dimethylbenzophenone, and 4-methyl-4'-benzophenonecarboxylic acid resulting from incomplete oxidation. The term precursor dialkyl aromatic hydrocarbon as used herein refers to an aromatic hydrocarbon containing two dialkyl groups which can be oxidized to carboxylic acid radicals, and in this particular instance, the corresponding dialkyl aromatic hydrocarbon could be 4,4'-diethylbenzophenone as well as 4,4'-dimethylbenzophenone. The term thus embraces all the possible hydrocarbons containing dialkyl groups, including those in which the alkyl groups are not identical, which can serve as a starting material by which the oxidation produces the desired aromatic dicarboxylic acid.

The term aromatic monocarboxylic acid genetic impurity as used herein refers to the intermediate oxidation products of the precursor dialkyl aromatic hydrocarbon which are the result of incomplete oxidation and the oxidation product of monoalkyl impurity in the precursor dialkyl aromatic hydrocarbon, both of which are undesirable in the final aromatic dicarboxylic acid product. Included in the term genetic impurity are high molecular weight aromatic monocarboxylic acids and alkyl aromatic monocarboxylic acids.

The 4,4'-benzophenonedicarboxylic acid has the following structural formula:

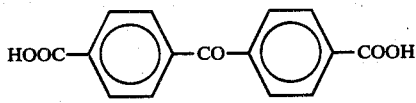

and the genetic impurities include those having the following structural formulas:

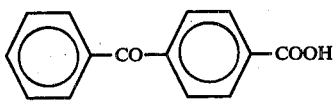

and

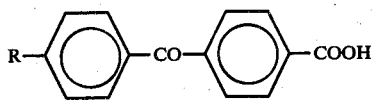

wherein R is an alkyl group, containing 1 to 8 carbon atoms and being linear or branched.

The purification procedure in general comprises dissolving impure 4,4'-benzophenonedicarboxylic acid, containing aromatic monocarboxylic acid genetric impurity in ammonium hydroxide solution to form a solution of the ammonium salt of the acid, removing undissolved impurities, e.g., by filtration, precipitating the ammonium salt of the acid by mixing the solution with a water soluble organic liquid, preferably acetone, and then recovering the purified material, usually by filtration followed by acidification of an aqueous solution of the precipitated ammonium salt and then isolating, washing and drying.

In general, the impure acid is dissolved in ammonium hydroxide solution containing about 28 weight percent or less of ammonia. It is preferred to use ammonium hydroxide solution containing about 4 to 14 weight percent of ammonia. The amount of ammonia used is not critical as long as a sufficient amount of ammonia is present to dissolve all the acid in the sample and sufficient water is present to keep the ammonium salt thus produced in solution. Optionally, in the procedure, the ammonium hydroxide solution of impure acid can be filtered if insoluble impurities are present, but this step can be omitted in the absence of insoluble impurities. Generally, 1 to 20 parts by weight of impure acid are used per 100 parts by weight of the ammonium hydroxide solution generally resulting in a 1 to 20 weight percent solution of dissolved ammonium salt of the acid in the ammonium hydroxide. However, it is preferred to use about 2 to 5 parts by weight of impure acid per 100 parts by weight of ammonium hydroxide solution.

Mixing of the aqueous solution of the ammonium salt of the acid with a water-soluble organic liquid is carried out either by adding the organic liquid to the aqueous solution of ammonium salt of the diacid or using the reverse procedure of adding the aqueous solution of ammonium salt of the diacid to the organic liquid. It is preferred to utilize the procedure of adding the water-soluble organic liquid to the aqueous solution of ammonium salt of the acid to in order to precipitate the ammonium salt of the aromatic dicarboxylic acid.

An important aspect of the invention is the weight ratio of organic liquid used to the aqueous solution of the ammonium salt of the acid. Generally, a ratio of about 0.4:1 to 20:1 parts by weight of organic liquid per part ammonium hydroxide solution is used. However, it is preferred to use a ratio of about 0.5:1 to 4:1 parts by weight of organic liquid per part ammonium hydroxide solution of the acid. Larger volumes will in general produce a higher yield and in general higher purity. However, very large volumes of organic liquid above 20:1 weight ratio of parts organic liquid per part solution are undesirable since impurities will also start to precipitate out at that point.

Organic liquids suitable for use in the invention process include those that are inert under the reaction conditions, are water-soluble, act as a non-solvent for the ammonium salt of the acid, contain from 1 to 10 carbon atoms, and contain functional groups including ketone, nitrile, ether and the like, but excluding carboxy. The organic liquids include aromatic solvents containing ring systems such as benzene and naphthalene, which may also contain one or more heterocyclic ring constituents such as N, O and S; aliphatic solvents, including carbon chains which are linear and branched alkyl, alkenyl, alkynyl, cycloalkyl and arylalkyl; and hydrogenated aromatic solvents, which may also contain one or more heterocyclic ring constituents such as N, O and S. Representative classes of solvents include linear and branched alkyl nitriles, cycloaliphatic ethers including cycloalkyl, cycloalkenyl ethers, and aliphatic ketones including linear and branched alkyl alkenyl and alkynyl ketones. Representative examples include tetrahydrofuran, dioxane, acetonitrile, acetone, methylethyl ketone and methylisobutyl ketone. It is preferred in the invention process, however, to use acetone.

By the term non-solvent for the ammonium salt is meant that no more than 5 percent by weight of the total amount of ammonium salt is soluble in the organic liquid.

After mixing together the organic liquid and the aqueous solution of ammonium salt of the acid, the contents are stirred whereupon the ammonium salt of the acid precipitates, is then isolated from the solution containing dissolved impurities, and collected by filtration. The acid can then be acidified with aqueous acid to produce the desired acid, which is then washed with water and dried. Optionally, the aromatic dicarboxylic acid can be recovered from the ammonium salt by heating in air.

If recovery of the purified acid is desired by acidification, this can be carried out with any acid capable of protonating the aromatic dicarboxylic acid without any adverse side reactions occuring. In general, one can use hydrochloric acid, sulfuric acid, phosphoric acid, nitric acid, acetic acid and trichloroacetic acid. However, it is preferred to use hydrochloric acid.

The purity of the obtained aromatic dicarboxylic acid is generally in the range of about 95 to 99.9 percent as measured by gas liquid chromatography.

The following example illustrates the process of the invention but should not be construed as limitations on the scope or spirit of the invention. Parts are by weight unless otherwise stated.

EXAMPLE

About 200 parts by weight of 4,4'-benzophenonedicarboxylic acid containing about 30 parts 4-methyl-4'-benzophenone-carboxylic acid as impurity, was treated with a mixture of 2000 parts of water and and 1000 parts of concentrated ammonium hydroxide. The mixture was stirred until the impure acid was substantially in solution. Cloudiness in the solution was due to impurities which were filtered off. The solution, after being filtered, was added slowly in a continuous stream in about 1.5 hours into 3000 parts of acetone with stirring. The ammonium salt of 4,4'-benzophenonedicarboxylic acid precipitated and was isolated by filtration. The precipitated ammonium salt was then treated with 2000 parts of water and stirred 15 to 20 minutes to dissolve and then was acidified by adding dilute hydrochloric acid until a pH of about 3 was reached. The 4,4'-benzophenonedicarboxylic acid precipitated, which was then filtered, washed with water and dried. Recovered were 150 parts of 4,4'-benzophenonedicarboxylic acid possessing a purity of about 99%, as determined by gas chromatography versus a standard sample.

We claim:

1. A process for purifying 4,4'-benzophenonedicarboxylic acid, containing aromatic monocarboxylic acid genetic impurity, which comprises the steps of
    (a) mixing the impure 4,4'-benzophenonedicarboxylic acid with aqueous ammonium hydroxide solution, containing about 28 weight percent or less of ammonia, in weight ratio of solution to acid of about 5:1 to 100:1 thereby forming an aqueous solution of the ammonium salt of the aromatic dicarboxylic acid;
    (b) removing insoluble impurities, if present, from the solution of the ammonium salt of the acid;
    (c) mixing the resultant solution with an inert water-soluble organic liquid, containing 1 to 10 carbon atoms and selected from the group consisting of aliphatic nitriles, cycloaliphatic ethers and aliphatic ketones, which is a non-solvent for the ammonium salt, in a weight ratio of organic liquid to solution not greater than about 20:1, thereby precipitating the ammonium salt of the acid;
    (d) separating the ammonium salt from the solution; and
    (e) recovering the aromatic dicarboxylic acid from the ammonium salt.

2. The process of claim 1 wherein the organic liquid is selected from the group consisting of acetonitrile, tetrahydrofuran, dioxane, acetone, methylethyl ketone and methylisobutyl ketone.

3. The process of claim 2 wherein the organic liquid is acetone.

4. The process of claim 1 wherein the weight ratio of organic liquid to ammonium hydroxide solution is about 0.5:1 to 4:1, and the weight ratio of ammonium hydroxide solution to impure acid is about 5:1 to 30:1.

5. The process of claim 1 wherein the ammonium hydroxide solution contains about 4 to 14 weight percent ammonia.

* * * * *